US009536720B2

(12) United States Patent
Sato et al.

(10) Patent No.: US 9,536,720 B2
(45) Date of Patent: Jan. 3, 2017

(54) ANALYZING APPARATUS (75) Inventors: Tomoyoshi Sato, Tsukuba (JP); Akira Imai, Tsukuba (JP)

(73) Assignee: ATONARP INC., Minato-Ku, Tokyo (JP)

( * ) Notice: Subject to any disclaimer, the term of this patent is extended or adjusted under 35 U.S.C. 154(b) by 0 days.

(21) Appl. No.: 13/881,915

(22) PCT Filed: Oct. 31, 2011

(86) PCT No.: PCT/JP2011/006104
§ 371 (c)(1),
(2), (4) Date: Jul. 10, 2013

(87) PCT Pub. No.: WO2012/056730
PCT Pub. Date: May 3, 2012

(65) Prior Publication Data
US 2013/0299694 A1   Nov. 14, 2013

(30) Foreign Application Priority Data

Oct. 29, 2010  (JP) .................................. 2010-243961

(51) Int. Cl.
*H01J 49/04* (2006.01)
*A61B 10/00* (2006.01)
(Continued)

(52) U.S. Cl.
CPC ............ *H01J 49/04* (2013.01); *A61B 5/4869* (2013.01); *A61B 10/0045* (2013.01);
(Continued)

(58) Field of Classification Search
CPC .... H01J 49/04; H01J 49/0409; H01J 49/0418; H01J 49/0431; H01J 49/044; H01J 49/0445; A61B 5/4869; A61B 10/02; A61B 10/0045
(Continued)

(56) References Cited

U.S. PATENT DOCUMENTS

2005/0133716 A1*  6/2005  Miller ................. G01N 27/624
                                                            250/293
2005/0139762 A1    6/2005  Miller et al.
(Continued)

FOREIGN PATENT DOCUMENTS

JP    2005-083784 A    3/2005
JP    2007-513340 A    5/2007
(Continued)

OTHER PUBLICATIONS

Morgner, et al. "A Novel Approach to Analyze Membrane Proteins by Laser Mass Spectrometry: From Protein Subunits to the Integral Complex", Journal of the American Society for Mass Spectrometry, 2007, 18, 1429-1438.*

(Continued)

*Primary Examiner* — David E Smith
(74) *Attorney, Agent, or Firm* — Buchanan Ingersoll & Rooney PC (57) ABSTRACT

There is provided an analyzing apparatus including an irradiation unit irradiating a first point with a laser, a convergence unit causing an analysis target to converge at the first point, and a unit analyzing a sample gas including a substance that has been irradiated with the laser at the first point using an ion mobility sensor. One example of the convergence unit includes a unit causing the analysis target to be captured in a carrier substance in a liquid state; and a discharging unit discharging the carrier substance including the analysis target to the first point.

12 Claims, 4 Drawing Sheets

(51) Int. Cl.
*A61B 5/00* (2006.01)
*A61B 10/02* (2006.01)
*G01N 33/497* (2006.01)
*G01N 1/02* (2006.01)
*G01N 27/62* (2006.01)

(52) U.S. Cl.
CPC .......... *A61B 10/02* (2013.01); *A61B 10/0051* (2013.01); *A61B 10/0064* (2013.01); *G01N 27/624* (2013.01); *G01N 33/497* (2013.01); *G01N 2001/028* (2013.01); *G01N 2800/20* (2013.01)

(58) Field of Classification Search
USPC ........................................ 250/281, 282, 288
See application file for complete search history.

(56) References Cited

U.S. PATENT DOCUMENTS

| | | | |
|---|---|---|---|
| 2005/0230615 A1* | 10/2005 | Furutani et al. ............. | 250/287 |
| 2006/0141544 A1* | 6/2006 | Anderson ........ | G01N 35/54306 435/7.23 |
| 2007/0003965 A1 | 1/2007 | Ramsay et al. | |
| 2009/0071815 A1* | 3/2009 | Takamizawa ......... | H01J 9/0059 204/157.15 |
| 2010/0288917 A1* | 11/2010 | Satulovsky ......... | H01J 49/0031 250/282 |
| 2011/0006196 A1 | 1/2011 | Boyle et al. | |
| 2011/0111513 A1* | 5/2011 | Baumann ........... | G01N 33/6848 436/89 |
| 2011/0204220 A1* | 8/2011 | Van Wuijckhuijse ... | G01N 1/38 250/282 |

FOREIGN PATENT DOCUMENTS

| | | |
|---|---|---|
| JP | 2007-279016 A | 10/2007 |
| JP | 2008-508693 A | 3/2008 |
| JP | 2008-157895 | 7/2008 |
| JP | 2008-547031 A | 12/2008 |
| WO | WO 2005/111594 A1 | 11/2005 |
| WO | 2006/137205 | 12/2006 |

OTHER PUBLICATIONS

Morgner et al, "A Novel Approach to Analyze Membrane Proteins by Laser Mass Spectrometry: From Protein Subunits to the Integral Complex", Journal of the American Society for Mass Spectrometry, 2007, 18, 1429-1438.*
International Preliminary Report on Patentability issued in corresponding PCT Application No. PCT/JP2011/006104 mailed May 10, 2013.
Official Action issued in corresponding Chinese Patent Application No. 2014110200461560, mailed Nov. 5, 2014.
Xian-Yun Liu et al. "Detection of Formaldehyde Using Ion Mobility Spectrometer With Laser Ionization Source", Journal of Optoelectornics—Laser, vol. 17, No. 12, Dec. 2006, pp. 1507-1509.
Qian Zhang et al. "Using of SELDI-TOF-MS for Serum Protein Markers in Patients With Hirschsprung's Disease".

* cited by examiner

ANALYZING APPARATUS

TECHNICAL FIELD

The present invention relates to an apparatus that analyzes chemical substances.

BACKGROUND ART

In recent years, attention has been focused on apparatuses called field asymmetric waveform ion mobility spectrometers (FAIMS) as a technology for detecting and analyzing chemical substances with high sensitivity. In such an apparatus, by changing the DC voltage and the AC voltage applied to sensors, it is possible to detect changes in the mobility of ionized chemical substances using a fine filter and to identify chemical substances according to differences in such detection results.

WO2006/013396 (Japanese Patent Publication No. 2008-508693) discloses an ion mobility spectrometer with an ion filter in the form of at least one ion channel that includes a plurality of electrodes. With this ion mobility spectrometer, it is possible for the filler to selectively input ion types according to the potential applied to the conductive layer that changes over time. Such potential has a drive electric field component and a transverse electric field component, and in a preferred embodiment, the respective electrodes contribute to the generation of both the drive electric field component and the transverse electric field component. Such device can be used even without a drift gas flow. In addition, such publication discloses a micromachining technology for manufacturing a microscale spectrometer for the various applications of a spectrometer.

DISCLOSURE OF THE INVENTION

It is important to be able to easily detect viruses and bacteria. However, it is rare for the measurement of microorganisms including viruses and bacteria to be carried out by analyzing apparatuses that use an ion mobility sensor.

One aspect of the present invention is an analyzing apparatus including: an irradiation unit irradiating a first point with a laser; a convergence unit causing an analysis target to converge at the first point; and a unit analyzing a sample gas including a substance that has been irradiated with the laser at the first point using an ion mobility sensor. Such analyzing apparatus is capable of destroying the analysis target through irradiation with a laser. Accordingly, for substances, such as microorganisms, that are too large to be detected and/or analyzed using an ion mobility sensor, it is possible, through irradiation with a laser, to cause break down to molecules that can be detected by an ion mobility sensor and thereby enable analysis.

The convergence unit may include: a unit causing the analysis target to be captured in a carrier substance in a liquid state; and a discharging unit discharging the carrier substance including the analysis target to the first point. It is possible to synchronize the timing for discharging the carrier substance and the timing of irradiation with the laser, and by doing so, it is possible to improve the efficiency with which the analysis target can be destroyed through irradiation with a laser. The discharging unit may include an ink jet head that discharges the carrier substance including the analysis target.

The carrier substance should preferably include a marker source material that releases a marker chemical substance by being irradiated with a laser. It is possible to determine that chemical substances that are detected together with the marker chemical substance by the ion mobility sensor are chemical substances derived from the analysis target.

One example of the marker source material includes a marker chemical substance and nanocapsules that encapsulate the marker chemical substance and release the marker chemical substance when irradiated with a laser. It is possible to provide nanocapsules that react with the energy level of laser irradiation which facilitates determination of the presence or absence of laser irradiation and derived substances of the analysis target formed due to such irradiation.

Another aspect of the present invention is an analyzing method including steps of:

causing an analysis target to converge at a first point irradiated with a laser; and analyzing a sample gas including a substance that has been irradiated with a laser at the first point using an ion mobility sensor.

Yet another aspect of the present invention is an analyzing method including steps of:

capturing an analysis target in a carrier substance in a liquid state;

discharging the carrier substance including the analysis target to the first point and irradiating the carrier substance with a laser. The carrier substance includes a marker source material that releases a marker chemical substance by being irradiated with a laser;

analyzing the sample gas including a substance irradiated with the laser at the first point using an ion mobility sensor; and determining a chemical substance detected together with the marker chemical substance by the ion mobility sensor as a chemical substance derived from the analysis target.

BRIEF DESCRIPTION OF THE DRAWINGS

FIG. 2 is output examples of the analyzing apparatus, where FIG. 2(a) is an example where a sample including a virus A has been analyzed and FIG. 2(b) is an example where a sample including a virus B has been analyzed.

DETAIL DESCRIPTION

Figure 1:
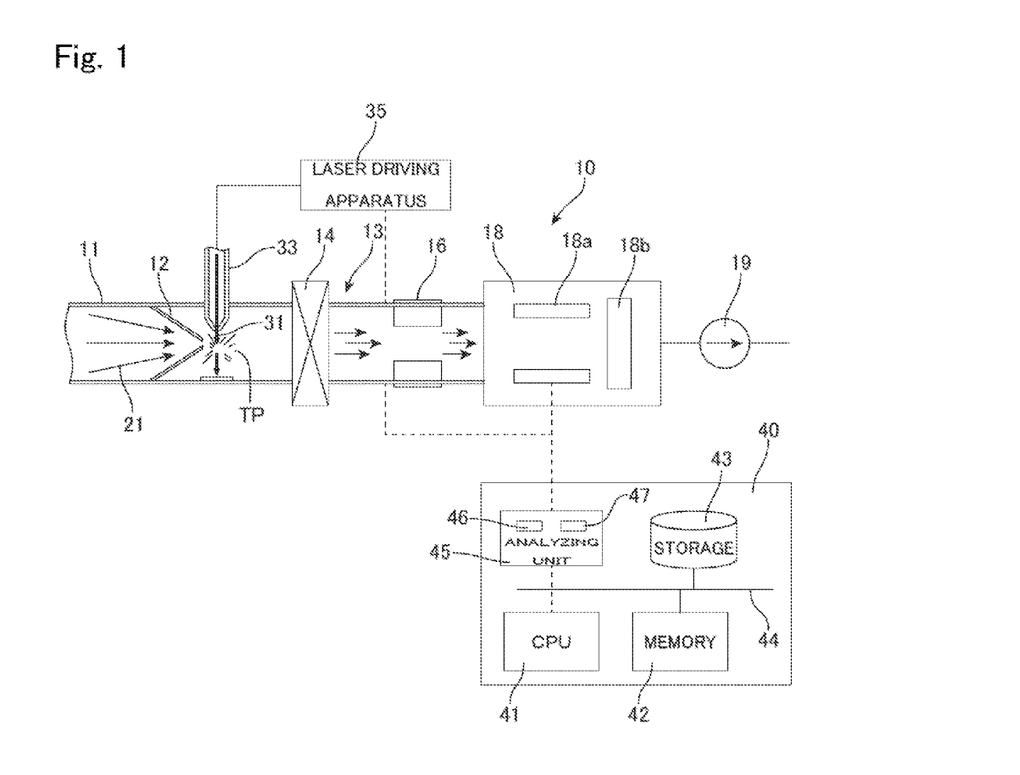
FIG. 1 is a block diagram showing configuration of an analyzing apparatus.

FIG. 1 shows one example of an analyzing apparatus. This analyzing apparatus 10 includes a sampling unit (sampling pipe or tube) 11 that collects room air (sample gas) 21, a cone-shaped guide vane (convergence unit) 12 that guides the sample gas 21 so as to converge on a first point TP where a laser is irradiated, a laser gun (irradiation unit) 33 that irradiates the first point TP with laser light 31, and a laser driving apparatus 35 that drives the laser gun 33 to output the laser light 31. The analyzing apparatus 10 also includes a supply path 13 that supplies the sample gas 21 after irradiation with the laser via a microfilter 14 and an ionizing unit 16 to an ion mobility sensor 18, and an exhaust pump 19 that draws in the sample gas 21.

The ion mobility sensor (ion mobility spectrometer) 18 outputs spectra (ion currents or ion intensities) based on differences in mobility between chemical substances (molecules) that have been ionized by the ionizing unit 16. The analyzing apparatus 10 includes an ion mobility sensor 18 called a FAIMS (Field Asymmetric waveform Ion Mobility Spectrometer) or a DMS (Differential ion Mobility Spectrometer). This type of spectrometer (or "sensor", hereinafter FAIMS) 18 forms an asymmetric electric field that changes from high voltage to low voltage in an electric field channel 18a and inputs ionized molecular flows into such asymmetric electric field. The ion current that passes such asymmetric electric field is then measured by the electrode 18b. The "micro DMx" made by SIONEX and the FAIMS device made by OWLSTONE can be given as examples of compact FAIMS that are commercially available.

One example of the ionizing unit 16 is an indirect ionizing unit that uses a nickel isotope (Ni63). The ionizing unit may be an ionizing unit that uses corona discharge or may be a direct ionizing unit that uses UV.

The analyzing apparatus 10 also includes a control apparatus, typically a personal computer (PC) 40. Control of the analyzing apparatus 10 and analysis of data obtained by the FAIMS sensor 18 are carried out by the PC 40. The PC 40 includes typical hardware resources that construct a computer, such as a CPU 41, a memory 42, storage 43 such as a hard disk drive, and a bus 44 that connects such components. In addition, the PC 40 includes an analyzing unit 45 that controls the analyzing apparatus 10 and analyzes data. The analysis unit 45 may be provided as a semiconductor device such as an ASIC or an LSI, or may be provided as a program (program product) executed by the CPU 41. The analyzing unit 45 includes a controller 46 that controls the laser driving apparatus 35, the FAIMS sensor 16, and an analyzer 47 that analyzes the data of the FAIMS sensor 18. The analyzing unit 45 may include a function that acquires environmental conditions such as the temperature, humidity, and pressure of the FAIMS sensor 18 via appropriate sensors and corrects the data obtained from the FAIMS sensor 18.

In the analyzing apparatus 10, the sample gas 21 flowing in the sampling tube 11 is concentrated (i.e., is caused to converge) at a limited location (area) by the guide vane 12, and such converging point TP is irradiated with a laser. Accordingly, viruses and/or bacteria or the like included in the sample gas 21, as well as cells included in the sample gas 21 and other macromolecules such as proteins can be destroyed (broken down) by the laser 31. The laser gun 33 may be any device capable of selectively severing specified parts of cells, proteins, or the like where the bond strength is weak, and may be a device capable of applying appropriate energy to the sample gas 21 via a laser, such as a UV laser or an X-ray laser. The broken-down substances pass through the microfilter 14 together with the sample gas 21, are ionized by the FAIMS sensor 16, and are detected by the FAIMS sensor 18.

Figure 2:
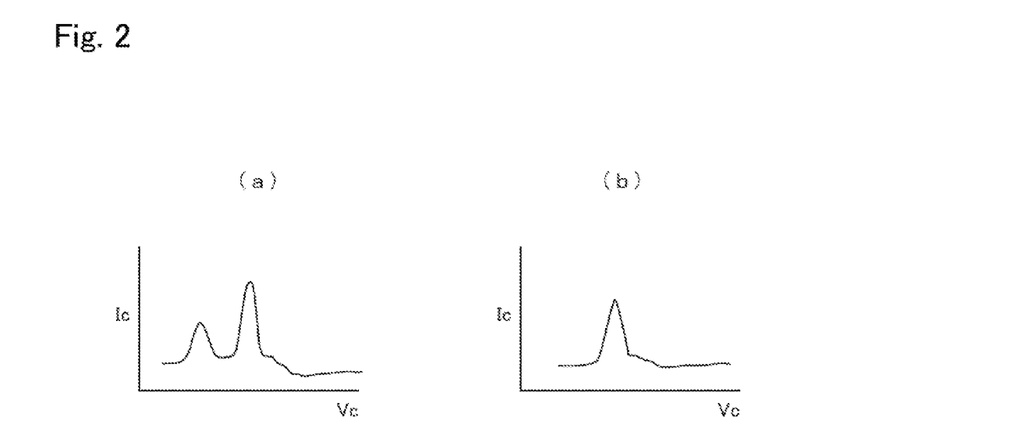

FIG. 2 shows a number of examples of spectra obtained by the FAIMS sensor 18. FIG. 2(a) is a spectrum obtained when the sample gas 21 including a virus A is irradiated with the laser 31 and FIG. 2(a) is a spectrum obtained when the sample gas 21 including a virus B is irradiated with the laser 31. Such spectra are exhibited by the ion current (ion intensity) Ic when the compensation voltage Vc of the FAIMS sensor 18 is changed.

Viruses, bacteria, macromolecular proteins, and the like are difficult to sufficiently ionize relative to their mass (molecular weight), which prevents easy detection by the FAIMS sensor 18. However, through irradiation with a laser, it is possible to cause breakdown into substances of a molecular weight that are capable of being ionized and to detect such substances using the FAIMS sensor 18. The analyzer 47 of the analyzing unit 45 analyzes data obtained from the FAIMS sensor 18 compares such data with chemical substances registered in a virus library stored in the storage 43 or the like, and searches for or estimates the virus that has been destroyed based on the chemical substances (derived substances) derived by breaking down a virus.

Microorganisms, such as viruses or bacteria, and macromolecules such as proteins (hereinafter collectively referred to as "microorganisms or the like") have a molecular structure and/or DNA structure that are somewhat regular. Accordingly, if microorganisms and the like are broken down by irradiation with a laser according to certain conditions, parts where the bond strength is weak are destroyed and extremely characteristic and distinguishable chemical substances (derived substances) are produced. Accordingly, in many cases a spectrum produced by the FAIMS sensor 18 analyzing a sample gas 21 in which microorganisms or the like have been broken down will be unique, and it will be possible to deduce or figure the microorganisms by verifying chemical substances included in the spectrum.

Figure 3:
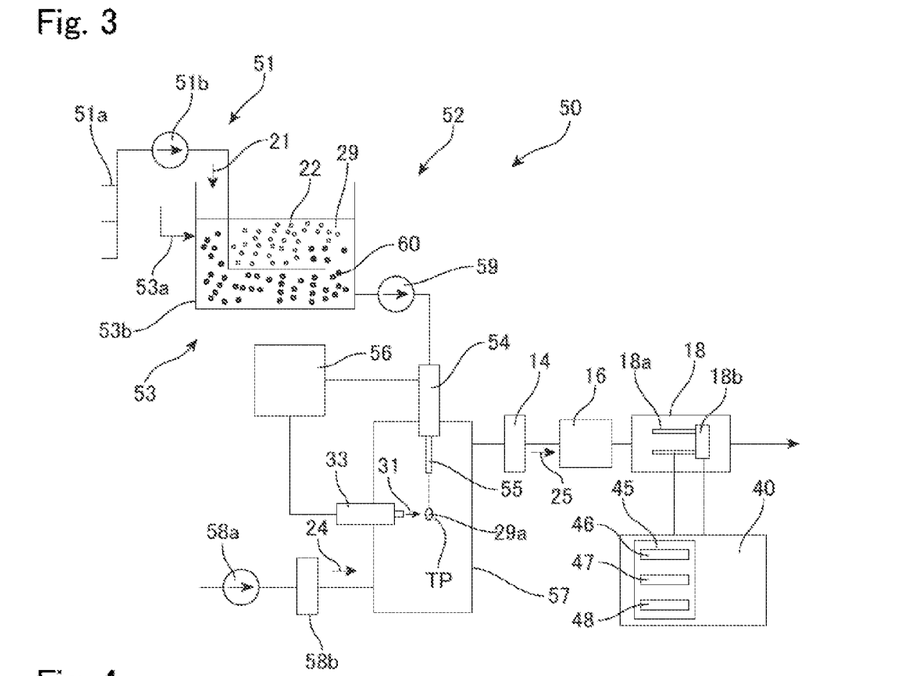
FIG. 3 is a block diagram showing configuration of a different analyzing apparatus.
Figure 4:
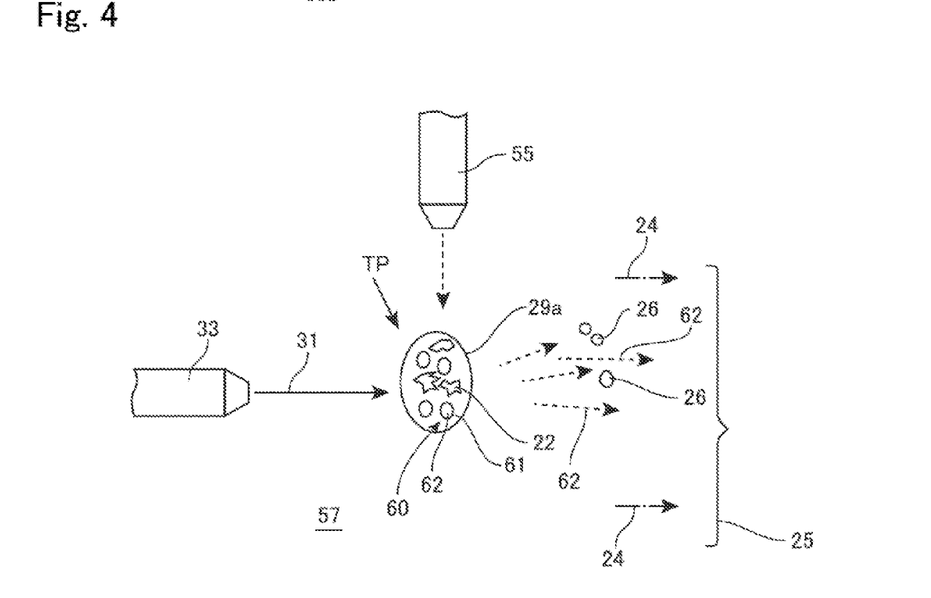
FIG. 4 is a diagram schematically showing how a discharged droplet is irradiated with a laser.
Figure 5:
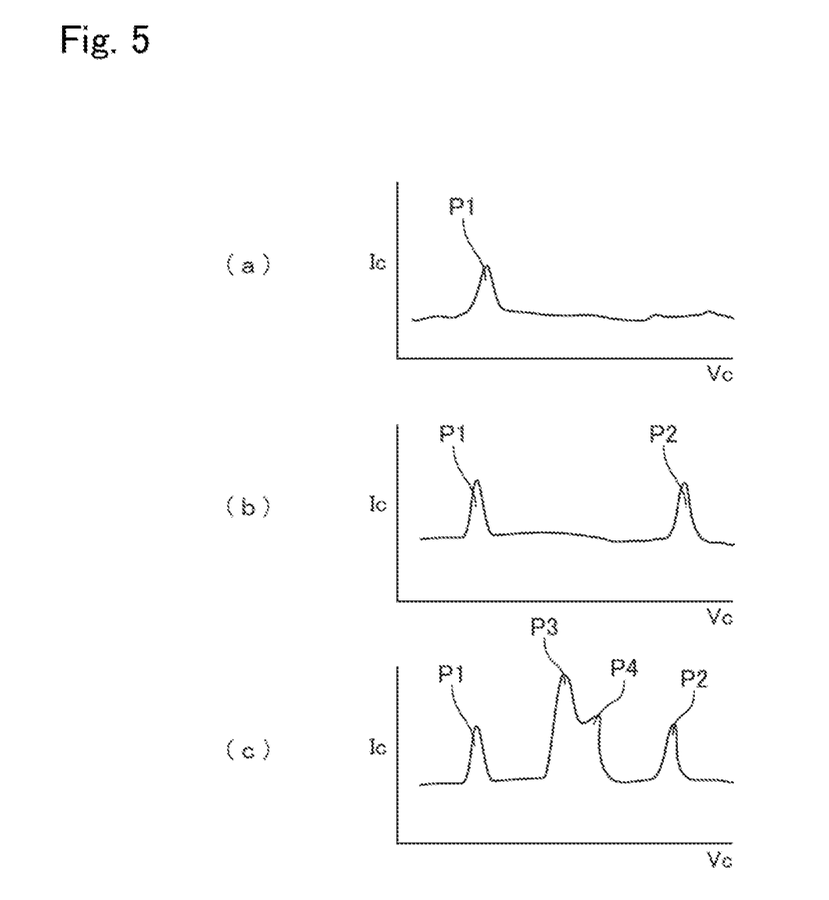
FIG. 5 shows output examples of the analyzing apparatus, with FIG. 5(a) the background, FIG. 5(b) an example where a marker substance is detected, and FIG. 5(c) an example where a derived substance is detected together with a marker substance.

FIG. 3 shows a different example of an analyzing apparatus. This analyzing apparatus 50 includes a sampling unit 51 that draws in primary sample gas 21 from a room or the like and a convergence unit 52 that causes the analysis target (that is, the microorganisms or the like) included in the sample gas 21 to converge at the first point TP and being irradiated with the laser. The sampling unit 51 includes a drawing nozzle 51a and a sampling pump 51b.

The convergence unit 52 includes a capture unit 53 that passes the primary sample gas 21 collected by the sampling pump 51b through a carrier substance 29 in liquid form to cause the microorganisms or the like 22 included in the sample gas 21 to be captured in the carrier gas 29, a discharge unit 54 that discharges the carrier substance 29 including the microorganisms or the like to the first point TP, and a pump 59 that conveys the carrier substance 29 to the discharge unit 54.

A typical example of a carrier substance 29 in liquid form is water, and in the capture unit 53, by bubbling the primary sample gas 21 in water, the microorganisms or the like 22 included in the primary sample gas 21 are concentrated in the water 21. The capture unit 53 includes a vessel 53b that mixes the microorganisms or the like 22 and the water 29 and a line 53*a* that supplies the water 29 to the vessel 53*b*. By supplying enough water 29 from the supply line 53*a* to regularly change the water inside the vessel 53*b* while keeping the water in the vessel 53*b* for a sufficiently long time, although there is the possibility of a slight delay, it will be possible to reflect the state of the microorganisms or the like 22 in a room or the like in the water 29 that is the carrier substance in close to a real-time state.

The carrier substance 29 further includes a marker source material 60. The marker source material 60 includes a marker chemical substance and nanocapsules in which such marker chemical substance is encapsulated. Nanocapsules are heated by irradiation with a laser and when a specified temperature is reached, the nanocapsules melt or sublimates and discharge the release the marker chemical substance. The nanocapsules should preferably have a size that is approximately the same as the microorganisms or the like 22 that are the analysis target, for example, microcapsules, submicrocapsules, or smaller capsules with a diameter of 0.1 to a few μm, more preferably around 1 to 1000 nm, and even more preferably 1 to 100 nm, with there being a number of methods of manufacturing such capsules. Polyurethane capsules that use polyvalent isocyanate and melamine-formaldehyde resin capsules are representative examples that use an interfacial polymerization method. In the case of capsules made of polyurethane, both the polyvalent isocyanate and the polyhydroxy compounds are dissolved at the same time into the oil phase, such substances are emulsified and dispersed in a protective colloid aqueous solution, then the temperature rises further, and a reaction occurs to form capsule walls. For capsules made of melamine-formaldehyde resin, a melamine-formaldehyde prepolymer that can be soluble in water is used. By adding such prepolymer solution to an O/W emulsion where an oil produced by melting a dye precursor has been emulsified and dispersed in a protective colloid aqueous solution and then heating and stirring in a weakly acidic region (with a pH of 3 to 6), polymer is deposited on the O/W interfaces, resulting in nanocapsules being obtained. As the protective colloid, it is possible to use a colloid that functions as an acid catalyst that promotes a polycondensation reaction of the melamine-formaldehyde resin (as examples, a styrene sulfonic acid polymer, a copolymer of styrene and maleic anhydride, a copolymer of ethylene and maleic anhydride, gum arabic, and polyacryl).

The marker substance should preferably be capable of being encapsulated in nanocapsules and of vaporizing when the nanocapsules melt away. In addition, the marker substance should preferably not have peaks that coincide when derived substances, which are produced by the microorganisms or the like 22 being broken down by the laser, are measured by the FAIMS sensor 18. Volatile hydrocarbon compounds and aromatic compounds are examples of marker substances.

Figure 6:
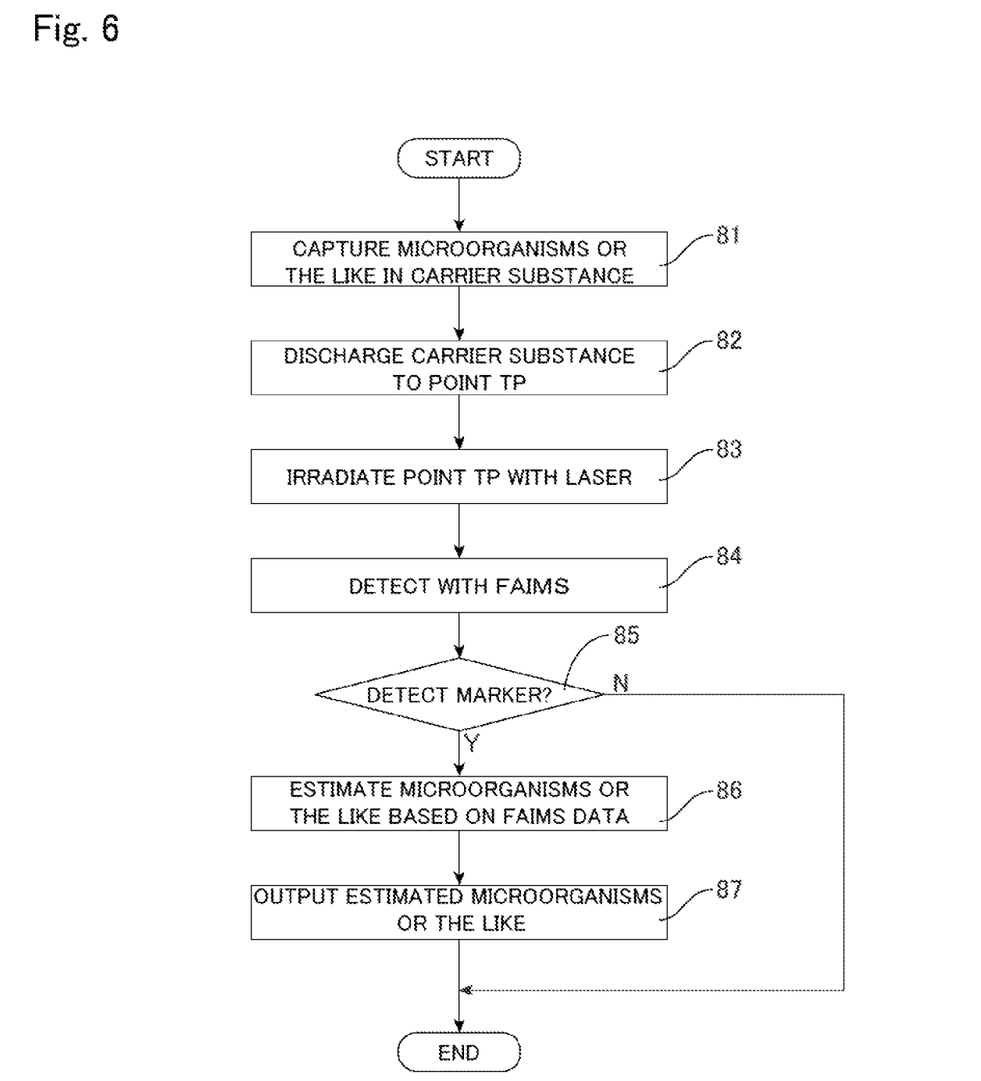
FIG. 6 is a flowchart showing an overview of the processing of the analyzing apparatus.

The discharge unit 54 includes an ink jet head 55 that discharges the carrier substance (water) 29 including the marker source material 60 and the microorganisms or the like 22 toward the first point TP and a head driving apparatus 56 that drives the ink jet head 55.

The analyzing apparatus 50 further includes a sealed chamber 57 that includes the first point TP where the ink jet head 55 discharges droplets and the laser gun (laser emission unit) 33 that irradiates the laser 31 toward the first point TP inside the chamber 57. The laser gun 33 is controlled by the head driving apparatus 56 so as to emit the laser 31 in synchronization with discharge of the ink jet head 55.

The analyzing apparatus 50 further includes a pump (fan, blower) 58*a* that supplies carrier gas 24 to the chamber 57 and a microfilter 58*b* that filters the carrier gas 24 supplied to the chamber 57. Inside the chamber 57, the droplets 29*a* of the carrier substance 29 including the microorganisms or the like 22 and the marker source material 60 are vaporized and destroyed by irradiation with the laser 31. In the same way as in the analysis apparatus described above, carrier gas (secondary sample gas) 25 including the destroyed substances passes the microfilter 14, is ionized by the ionizing unit 16, and is analyzed by the FAIMS sensor 18.

FIG. 4 schematically shows how a droplet 29*a* of the carrier substance 29 is irradiated with the laser 31 inside the chamber 57. When a droplet 29*a* is discharged from the ink jet head 55, in synchronization with the discharge timing, the laser 31 is emitted from the laser gun 33 so as to strike the droplet 29*a* at the first point TP. When the laser 31 strikes the droplet 29*a*, the carrier substance 29 that constructs the droplet 29*a* in picoliter or femtoliter units vaporizes, also the laser 31 strikes and melts or breaks down the marker source material 60 and the microorganisms or the like 22 included in the droplet 29*a*.

The nanocapsules 61 of the marker source material 60 are constructed of a material that melts or breaks down rapidly due to the energy of the irradiated laser 31. Accordingly, the nanocapsules 61 struck by the laser 31 melt away and the marker substance 62 encapsulated in the nanocapsules 61 is released. At the same time, the microorganisms or the like 22 are also destroyed or broken down by the laser 31, and chemical substances (derived substances) 26 derived from the microorganisms or the like 22 are formed. Such materials are released together with the carrier gas (typically air) 24 from the chamber 57 as the secondary sample gas 25.

The laser gun 33 may emit the laser in units of picoseconds or femtoseconds. By emitting a femtosecond-pulsed laser, it is possible to destroy and disperse molecules more precisely so as to generate derived substances without vaporization or sublimation of the microorganisms or the like 22. Also, in the same way as MALDI (Matrix Assisted Laser Desorption/Ionization), it is possible to add an agent, for example, metallic powder, that absorbs laser light to the carrier substance 29 and thereby suppress vaporization of the microorganisms or the like 22 by the laser light.

FIG. 5 shows examples of outputs (spectra) of the FAIMS sensor 18 obtained by the analyzing unit 45 of the PC 40. The spectrum in FIG. 5(*a*) is one example of the background, where a peak (RIP) P1 showing the moisture in the air can be seen. The spectrum in FIG. 5(*b*) is an example of the secondary sample gas 25 obtained when droplets 29*a* of the carrier substance are irradiated with the laser 31. The marker source material 60 included in the droplets 29*a* is irradiated by the laser 31 and a peak P2 appears due to the releasing of the marker substance 62.

The spectrum in FIG. 5(*c*) is another example of the secondary sample gas 25 obtained when the droplets 29*a* of the carrier substance are irradiated with the laser 31. In addition to the peak P2 of the marker substance 62 produced by irradiating the marker source material 60 included in the droplets 29*a* with the laser 31, peaks P3 and P4 of the chemical substances that are derived substances (fragments) produced by irradiation of the microorganisms or the like 22 with the laser 31 appear.

The analyzing unit 45 shown in FIG. 3 includes a function (function unit) 48 that determines that the peaks P3 and P4 of chemical substances detected together with the peak P2 of the marker chemical substance by the FAIMS sensor 18 are chemical substances derived from the microorganisms or the like 22 that are the analysis target. Accordingly, if the determining function 48 has determined or recognized peaks of chemical substances formed from the microorganisms or the like 22, the analyzer 47 of the analyzing unit 45 estimates the chemical substances based on the peaks P3 and P4 and identifies that the microorganisms or the like 22 comprising such chemical substances were included in the primary sample gas 21.

The analyzer 47 uses a chemical substance library stored in the storage 43 and/or another database or library capable of being accessed via a computer network or the Internet, to analyze the chemical substances and find the microorganisms or the like 22 from which such chemical substances were derived using a method such as various fitting methods, simulated annealing, mean field annealing, a genetic algorithm, and a neural network. Note that parts of the construction of the analyzing apparatus 50 that are the same as the analyzing apparatus 10 have been assigned the same reference numerals and description thereof is omitted.

FIG. 6 shows an overview of a process where the analyzing apparatus 50 analyzes sample gas by way of a flowchart. In step 81, the primary sample gas 21 including the microorganisms or the like 22 that are to be analyzed is collected and captured in the liquid carrier substance (water) 29 by the capture unit 53. Next, in step 82, the carrier substance including the microorganisms or the like 22 is discharged toward the first point TP using the discharge unit 54 that includes the ink jet head 55 and in synchronization with such timing, in step 83 the laser gun 33 emits the laser 31 toward the first point TP.

In step 84, the secondary sample gas 25 including the substances that have been irradiated with the laser is analyzed by the FAIMS sensor 18. If the marker substance 62 is detected in step 85, the determining function 48 determines that the peaks P3 and P4 detected together with the marker chemical substance 62 are chemical substances derived from the microorganisms or the like 22 and in step 86, the analyzer 47 estimates or deduces the microorganisms or the like 22 included in the sample gas 21 from the chemical substances. In step 87, the PC 40 then outputs the estimated or deduced microorganisms or the like 22 using the display function of the PC 40 or outputs to an external machine or the like via a computer network such as the Internet.

Note that although an example where the microorganisms or the like 22 are captured in a liquid carrier substance 29 with a marker source material has been described, the carrier substance 29 itself may not be water and instead be a marker substance itself that produces a smell, such as an organic solvent. In addition, the carrier substance 29 may be a material that can be converted to a marker substance by vaporization caused by irradiation with a laser. It is also unnecessary to sample the sample gas including the microorganisms or the like in real time and the sample gas may be sampled using an appropriate sampler at a location that is temporally or spatially separated from the analyzing apparatus.

In many fields such as food processing, medicine, and the dairy sector, it is extremely important to detect and analyze various viruses and bacteria. However, in the past, since it was difficult to specify microorganisms or the like by applying a FAIMS sensor, such microorganisms or the like have often been avoided as measurement subjects of a FAIMS sensor. According to the present invention, the benefit of being able to specify viruses and bacteria to prevent food contamination, nosocomial infection, and nosocomial contamination and in other medical fields in real time or close to real time is immeasurable.

In the analyzing apparatuses described above, by using an ion mobility sensor such as a FAIMS sensor, it is possible to detect the presence of microorganisms or the like and to deduce the types of microorganisms or the like in real time or close to real time. Also, in addition to the viruses and bacteria included in the sample gas, by destroying (breaking down) macromolecules such as proteins, this analyzing apparatus enables such macromolecules to be easily detected using an ion mobility sensor. Accordingly, in the same way as other chemical substances, it is possible to carry out characterization of a plurality of viruses, bacteria, proteins, and the like based on information on ion mobility and the like obtained from an ion mobility sensor. Also, by constructing a database including information produced by characterization, it becomes possible to estimate and specify a plurality of viruses, bacteria, proteins, and the like using software.

The invention claimed is:

1. An analyzing apparatus comprising:
a convergence unit including a discharging unit that discharges to a first point droplets of a carrier substance in a liquid state including an analysis target and a source material that releases a first chemical substance when irradiated with a pulsed laser, the first chemical substance showing the source material is irradiated with the pulsed laser;
an irradiation unit irradiating the first point with the pulsed laser in synchronization with timing at which the discharging unit discharges the droplets; and
an analyzing unit analyzing a sample gas including a substance that has been irradiated with the pulsed laser at the first point, the analyzing unit using a sensor that outputs spectrum data;
wherein the first chemical substance is released and thus detectable by the sensor using at least one peak that does not coincide with peaks of the analysis target when the carrier substance is irradiated by the pulsed laser irrespective of the analysis target existing in the carrier substance;
wherein the analyzing unit includes a processor configured to:
detect whether a peak of the first chemical substance is included in the output spectrum data; and
when the analyzing unit detects the at least one peak of the first chemical substance is included in the output spectrum data, the analyzing unit determines the output spectrum data was caused by irradiation of the first chemical substance with the pulsed laser, and the analyzing unit identifies one or more peaks except for the at least one peak of the first chemical substance included in the spectrum data caused by irradiation of the analysis target with the pulsed laser.

2. The analyzing apparatus according to claim 1,
wherein the convergence unit includes a unit causing the analysis target to be captured in a carrier substance, and the discharging unit includes an ink jet head.

3. The analyzing apparatus according to claim 2,
wherein the irradiation unit controls energy supplied to the droplets discharged by the ink jet head so that the carrier substance vaporizes without vaporization or sublimation of the analysis target.

4. The analyzing apparatus according to claim 1,
wherein the source material includes:
a first chemical substance; and
nanocapsules that encapsulate the marker chemical substance and release the first chemical substance when irradiated with a laser.

5. The analyzing apparatus according to claim 1, wherein the sensor is an ion mobility sensor.

6. The analyzing apparatus according to claim 1, wherein the sensor is field asymmetric waveform ion mobility spectrometer.

7. The analyzing apparatus according to claim 1, wherein the sensor is a differential ion mobility spectrometer.

8. The analyzing apparatus according to claim 1, wherein the analyzing unit uses a chemical substance database to identify the analysis target from the one or more peaks of the analysis target included in the output spectrum data.

9. An analyzing method comprising:
irradiating a first point with a pulsed laser in synchronization with timing at which a discharging unit discharges droplets of a carrier substance in a liquid state including an analysis target and a source material that releases a first chemical substance when irradiated with the pulsed laser, the first chemical substance showing the source material is irradiated with the pulsed laser; and analyzing a sample gas including a substance that has been irradiated with the laser at the first point using a sensor that outputs spectrum data, wherein the first chemical substance is released and thus detectable by the sensor using at least one peak that does not coincide with peaks of the analysis target when the carrier substance is irradiated by the pulsed laser irrespective of the analysis target existing in the carrier substance;

wherein the analyzing the sample gas includes distinguishing between a background spectrum and a spectrum data that includes spectrum of the analysis target produced when the droplets are irradiated with the pulsed laser according to whether a peak of the first chemical substance is included in spectrum data together with the spectrum of the analysis target.

10. The analyzing method according to claim 9, wherein the analyzing unit is further configured to determine that a chemical substance detected together with the first chemical substance from the spectrum of the analysis target included in the spectrum data with a peak of the first chemical substance is a chemical substance derived from the analysis target, wherein the irradiating the first point with the pulsed laser includes controlling the energy supplied to the droplets discharged by an ink jet head included in the discharging unit so that derived substances are generated without vaporization or sublimation of the analysis target.

11. The analyzing method according to claim 9, wherein the analyzing includes detecting whether a peak of the marker chemical substance is included in the output spectrum data; and when the analyzing unit detects a peak of the marker chemical substance is included in the output spectrum data, the analyzing unit identifies one or more peaks of the analysis target included in the output spectrum data.

12. The analyzing method according to claim 9, wherein the sensor is a field asymmetric waveform ion mobility spectrometer.

* * * * *